United States Patent [19]
Higgins et al.

[11] Patent Number: 5,666,977
[45] Date of Patent: Sep. 16, 1997

[54] ELECTRICAL SMOKING ARTICLE USING LIQUID TOBACCO FLAVOR MEDIUM DELIVERY SYSTEM

[75] Inventors: Charles T. Higgins, Richmond; Wynn R. Raymond, Chesterfield; Francis M. Sprinkel, Glen Allen, all of Va.

[73] Assignee: Philip Morris Incorporated, New York, N.Y.

[21] Appl. No.: 378,881

[22] Filed: Dec. 23, 1994

Related U.S. Application Data

[63] Continuation of Ser. No. 74,948, Jun. 10, 1993, abandoned.

[51] Int. Cl.⁶ .................................................. A24F 47/00
[52] U.S. Cl. ..................... 131/194; 131/273; 128/200.14; 128/202.21; 128/203.27
[58] Field of Search ........................... 131/270–273, 131/194; 239/135, 102.2; 261/DIG. 65; 128/202.21, 200.14, 203.27

[56] References Cited

U.S. PATENT DOCUMENTS

| | | | |
|---|---|---|---|
| 4,334,531 | 6/1982 | Reichl et al. | 128/200.14 |
| 4,682,010 | 7/1987 | Drapeau et al. | 128/203.27 X |
| 4,719,476 | 1/1988 | Elrod et al. | 239/102.2 |
| 4,719,480 | 1/1988 | Elrod et al. | 239/102.2 |
| 4,735,217 | 4/1988 | Gerth et al. | 131/273 |
| 4,877,989 | 10/1989 | Drews et al. | 310/323 |
| 5,038,769 | 8/1991 | Krauser | 128/203.27 |
| 5,078,976 | 1/1992 | Shibauchi et al. | 261/DIG. 65 X |
| 5,144,962 | 9/1992 | Counts et al. | 128/203.27 X |
| 5,338,688 | 8/1994 | Deeg et al. | |

FOREIGN PATENT DOCUMENTS

| | | |
|---|---|---|
| 2017366 | 11/1990 | Canada . |
| 37 35 704.2 | 10/1987 | Germany . |
| WO 90/01997 | 3/1990 | WIPO . |

*Primary Examiner*—Jennifer Bahr
*Attorney, Agent, or Firm*—Charles E. B. Glenn; James E. Schardt; James T. Moore

[57] ABSTRACT

A smoking article and method is provided in which a liquid tobacco flavor generating system is used to deliver a liquid tobacco flavor medium to a heater to generate a predetermined quantity of tobacco flavor substance for delivery to a smoker. The article includes an electrical heating means, a tobacco flavor medium delivery system, a source of electrical energy and a control means to generate the tobacco flavor substance for delivery to a smoker.

27 Claims, 15 Drawing Sheets

5,666,977

ELECTRICAL SMOKING ARTICLE USING LIQUID TOBACCO FLAVOR MEDIUM DELIVERY SYSTEM

RELATED APPLICATIONS

This is a continuation of U.S. Ser. No. 08/074,948 filed Jun. 10, 1993, which is abandoned.

BACKGROUND OF THE INVENTION

This invention relates to articles in which a tobacco flavor medium is heated to release tobacco flavors. More particularly, this invention relates to an electrical smoking article in which the tobacco flavor medium is a liquid.

Electrical smoking articles are well known. Such articles generally include a plurality of electrical heating elements disposed adjacent tobacco flavor medium containing, for example, tobacco or tobacco-derived material. In such smoking articles the plurality of heating elements can be either disposable (see, e.g., commonly-assigned U.S. Pat. Nos. 5,060,671 and 5,095,921, which are hereby incorporated by reference in their entirety) or permanent (see, e.g., copending, commonly-assigned United States patent application Ser. No. 07/943,504, which is hereby incorporated by reference in its entirety). The tobacco flavor medium may be, for example, a solid material that is inserted into a cavity of the electrical smoking article. If the heaters are disposable, then the tobacco flavor medium would be deposited on the electrical heating elements that are inserted. After a finite number of "puffs" on the article by the smoking (e.g., eight or ten), the tobacco flavor medium, along with the electrical heating elements if disposable, is removed from the cavity and replaced with fresh tobacco flavor medium (and heaters).

It has been found that with the types of electrical smoking articles described above, the number of puffs available to the smoker for each loading of tobacco flavor medium is generally limited by the number of heating elements in the smoking article. For example, if the smoking article has eight heaters, then a smoker will derive eight puffs before having to replace the used tobacco flavor medium with fresh tobacco flavor medium (and heaters).

Additionally, because the above smoking articles have a plurality of heaters, the design and manufacture of such smoking articles can be complicated. For example, the plurality of heaters generally must be spaced sufficiently far apart from each other that each heater is thermally isolated from the other heaters. Also, the total number of heaters that can be placed in the smoking article may be limited since increasing the number of heaters generally results in an increase in the volume of the smoking article.

Furthermore, the physical arrangement of the plurality of spaced-apart heaters may also complicate placement of the tobacco flavor generating material which generally must be placed in thermal communication with each heater. In particular, the shape and construction of the tobacco flavor medium may be limited by the arrangement of the plurality of heaters. For example, the tobacco flavor generating material would have to extend over a volume that reaches each individual heater. This can result in the use of a greater volume of tobacco flavor generating material than is actually heated by the heaters and, thus, may result in the waste of tobacco flavor generating material that is not heated. Also, such excess tobacco flavor generating material may serve as a heat sink which may unnecessarily increase the power consumption of the article.

In light of the above, it would therefore be desirable to be able to provide an electrical smoking article in which the number of puffs from the smoking article is not limited by the number of heating elements.

It would also be desirable to be able to provide such a smoking article in which the design and manufacturing of the smoking article is simplified.

It would further be desirable to be able to provide such a smoking article in which the amount of tobacco flavor medium that is wasted is reduced.

SUMMARY OF THE INVENTION

It is an object of this invention to provide an electrical smoking article in which the number of puffs from the smoking article is not limited by the number of heating elements.

It is also an object of this invention to provide such a smoking article in which the design and manufacturing of the smoking article is simplified.

It is a further object of this invention to provide such a smoking article in which the amount of tobacco flavor medium that is wasted is reduced.

In accordance with this invention, there is provided an electrical smoking article for delivering to a smoker a tobacco flavor substance. The smoking article includes an electrical heating means, a tobacco flavor medium delivery system including an inlet adapted to be coupled to a liquid tobacco flavor medium cartridge and an outlet having one or more openings adapted for dispensing liquid tobacco flavor medium toward the heating means, and a means coupled between the inlet and outlet and adapted to transfer a predetermined amount of liquid tobacco flavor medium from the liquid tobacco flavor medium cartridge to the one or more openings. When the electrical heating means is activated, a predetermined amount of liquid tobacco flavor medium is dispensed from the outlet and is heated, generating a predetermined quantity of tobacco flavor substance for delivery to the smoker.

In accordance with the present invention, a method for delivering to a smoker a tobacco flavor substance is also provided. The method includes the step of transferring a predetermined amount of liquid tobacco flavor medium from a liquid tobacco flavor medium cartridge to an outlet. The outlet is adapted to dispense the liquid towards an electrical heater. The method also includes the step of activating the heater so as to heat the predetermined amount of liquid tobacco flavor medium dispensed from the outlet and subsequently generate a predetermined quantity of tobacco flavor substance for delivery to the smoker.

BRIEF DESCRIPTION OF THE DRAWING

The above and other objects and advantages of the present invention will be apparent upon consideration of the following detailed description, taken in conjunction with accompanying drawings, in which like reference characters refer to like parts throughout, and in which.

DETAILED DESCRIPTION OF THE INVENTION

Figure 1:
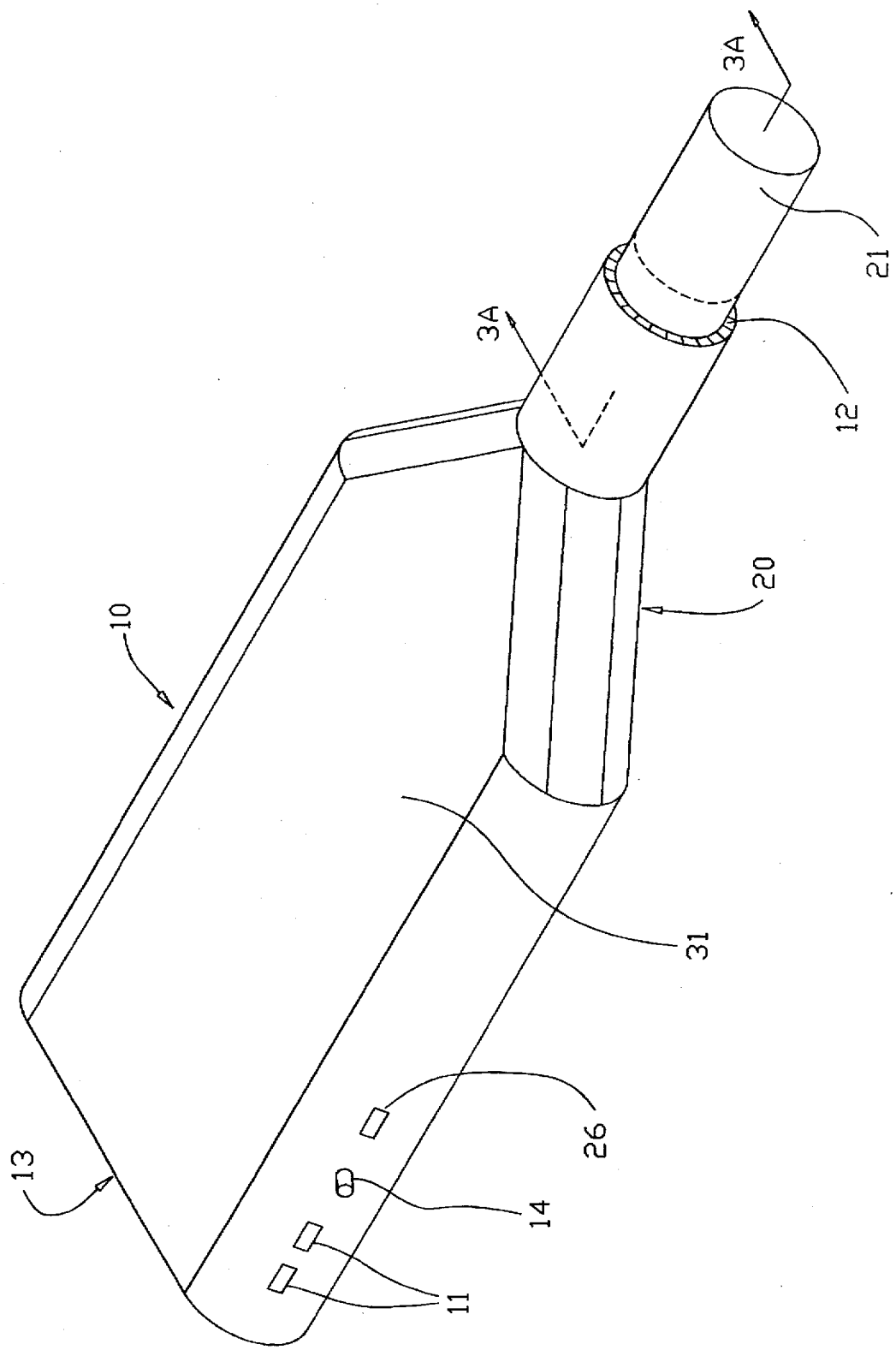
FIG. 1 is a perspective view of a first preferred embodiment of an electrical smoking article according to the present invention.
Figure 2:
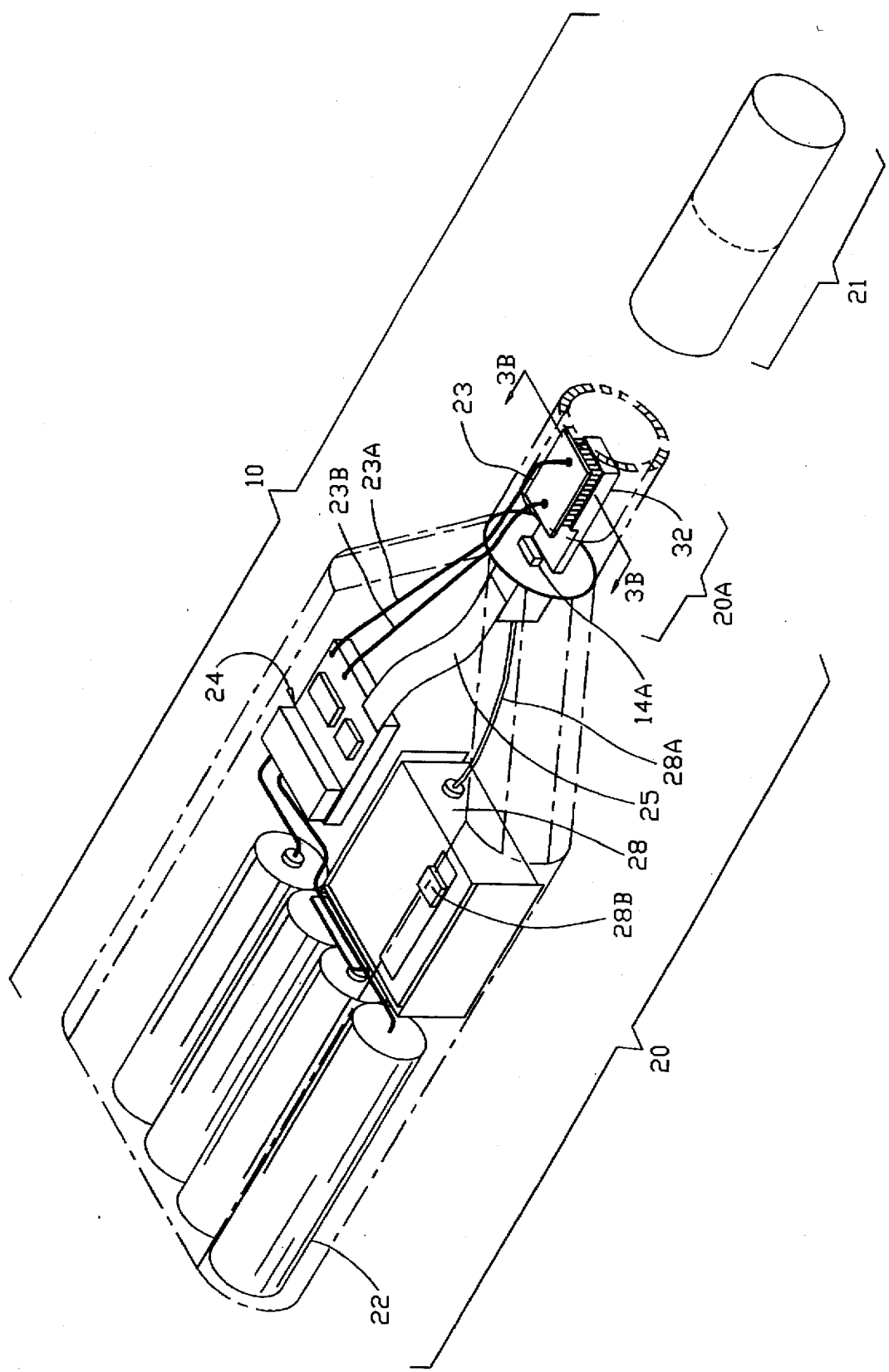
FIG. 2 is a partially fragmentary exploded perspective view of the electrical smoking article of FIG. 1.

The electrical smoking article of the present invention includes a liquid tobacco flavor medium delivery system for transferring the liquid tobacco flavor medium from a preferably replaceable liquid medium cartridge to a heater for subsequent generation of a predetermined quantity of tobacco flavor substance for delivery to a smoker. Such an electrical smoking article can be used, for example, to simulate a cigarette. In such a case, the liquid tobacco flavor medium would be a liquid material containing cigarette tobacco or cigarette tobacco derivatives.

The replaceable liquid medium cartridge of the electrical smoking article of the present invention is inserted into a reusable "permanent" portion including a source of electrical energy, a permanent heating element, and control circuitry for energizing the heater, in response to manual actuation or puff-induced actuation. Preferably, the present invention also includes control circuitry for delivering a predetermined amount of electrical energy to the heater upon actuation, independent of the power supply loaded voltage. Suitable control circuitry is described in more detail below and in above-incorporated U.S. patent application Ser. No. 07/943,504.

The reusable or permanent portion preferably includes a permanent cavity at the mouth end thereof for insertion of a preferably disposable filter unit for providing desirable pressure drop, air flow and filtration for flavor delivery to the smoker. A permanent heater preferably is disposed in the permanent cavity in liquid transfer relationship with the liquid tobacco flavor medium delivery system of the present invention.

The liquid tobacco flavor medium which is contained within the replaceable liquid medium cartridge of the present invention can be any liquid material that liberates tobacco flavors when heated and is able to be delivered to the permanent heater by the liquid tobacco flavor medium delivery system. Such liquid materials may or may not contain tobacco or tobacco-derived materials. It is desirable, however, that the liquid tobacco flavor medium contain an aerosol precursor so that when the tobacco flavor medium is heated to form the tobacco flavor substance, the substance formed is an aerosol. When the smoker exhales such a tobacco flavor substance, a visible condensed aerosol may mimic the appearance of conventional cigarette smoke.

In electrical smoking articles with a plurality of heaters, when any given heater is activated, any of the remaining inactivated cool heaters may be susceptible to condensation of aerosol. Subsequent heating of those remaining heaters may result in the generation of undesirable compounds, including off-tastes, if aerosol condensation is significant. In the preferred embodiment of the present invention, with only one permanent heater, there is no cool heater on which aerosol can condense. Although residual aerosol may remain after the heater cools, and thus may condense on the heater, the amount of such condensation is negligible. In any event, if desired, such residual aerosol which condenses onto the permanent heater of the present invention can be at least partly removed by heating the heater without activating the liquid delivery system.

The parameters of the permanent heater are chosen to allow delivery of an effective amount of tobacco flavor substance—e.g., an aerosol containing tobacco flavors—to the smoker under standard conditions of use. For example, it may be desirable to deliver 1 mg to 2 mg of aerosol to a smoker during a 35 ml puff having a two-second duration.

In order to achieve such delivery, the heater should preferably be able to reach a temperature of between about 200° C. and about 700° C., more preferably between about 300° C. and about 450° C. Furthermore, the heater should preferably consume between about 5 Joules and 40 Joules of energy.

The material of which the heater is made is preferably chosen to assure reliable repeated uses and is also chosen based on its reactivity, to assure that it will not react with the liquid tobacco flavor medium at any temperature likely to be encountered to form any undesired compounds. Similarly, the heater itself should not evolve any undesired compounds even when heated out of the presence of the tobacco flavor medium. Alternatively, a heater that might otherwise evolve undesired compounds could be encapsulated in an inert heat-conducting material such as a suitable ceramic material.

Based on these criteria, preferred materials for the heater of the present invention include silicon, carbon, graphite, stainless steel, tantalum, metal ceramic matrices, and metal alloys, such as iron alloys, and nickel-chromium alloys. Suitable metal-ceramic matrices include silicon carbide aluminum and silicon carbide titanium. Of the listed materials, stainless steel and the iron or chromium alloys should preferably be encapsulated in a suitable ceramic material because of their poor oxidation and corrosion resistance at high temperatures. Suitable ceramic materials for encapsulation include silica, alumina, and sol gels.

A first preferred embodiment of an electrical smoking article 10 according to the present invention is shown in FIGS. 1–4. Smoking article 10 includes reusable or "permanent" portion 20 and disposable filter insert 21 which is received in a permanent cavity 30 at the mouth end of portion 20. Portion 20 of the embodiment shown in FIGS. 1–4 includes liquid jet delivery system 32, power source 22, heater 23, control circuit 24 and liquid medium cartridge 28.

Power source 22, at the end remote from the mouth end, could include a battery, a capacitor or both. The battery could be replaceable, rechargeable or both. If the battery is rechargeable, or if the power source 22 is a capacitor alone, then article 10 is provided with charging contacts 11 on its outer surface, for connection to an external power supply (not shown) for charging power source 22. Power source 22 provides power for heater 23 (through heater leads 23A and 23B), which preferably is activated by puff-actuated sensor 14A. In the alternative, control circuit 24 is actuated by pushbutton 14.

Indicator 26, which could be a light-emitting diode, seven-segment liquid crystal display or other visual indicator, indicates the status of the amount of liquid tobacco flavor medium left in liquid medium cartridge 28 and, if desired, the status of power source 22 (e.g., whether it needs to be recharged, whether it has been fully recharged during recharging, or an approximation of the amount of charge remaining).

Power source 22 also provides power (through electrical connector 25) for liquid jet delivery system 32 which operates under the control of control circuit 24. Liquid jet delivery system 32 includes one or more nozzles 33 (FIG. 3). Delivery tube 28A connects to liquid jet delivery system 32. Nozzles 33 are oriented towards heater 23 and spray a predetermined amount of liquid tobacco flavor medium, in the form of droplets, towards heater 23. Heater 23 subsequently heats the droplets to generate aerosol which is then drawn through preferably disposable filter insert 21 for delivery to the smoker. If desired, heater 23 can be activated just prior to activation of liquid jet delivery system 32 to allow time for the heater to reach its operating temperature before it is sprayed with liquid tobacco flavor medium.

Preferably, replaceable liquid medium cartridge 28 should have a volume capable of holding at least enough liquid to provide about 160 puffs by a smoker before having to replace the cartridge. In order to replace cartridge 28, lock 28B is slid to an unlocked position to allow removal of cartridge 28. A puncture device (not shown) attached to medium delivery tube 28A can be used to puncture a seal in each newly-inserted cartridge 28 to allow liquid flow from cartridge 28 to liquid jet delivery system 32.

Portion 20 is covered by removable housing 31. Housing 31 is comprised of heat-resistive heavy paper, plastic or aluminum. Air flow channels 12 may be provided in region 20B of cylindrical wall portion 20A of portion 20 to allow outside air to be drawn in during puffing (see FIG. 3A). Air flow channels 12 are adapted to provide the air flow contours labelled "AR" in FIG. 3A.

Figure 3A:
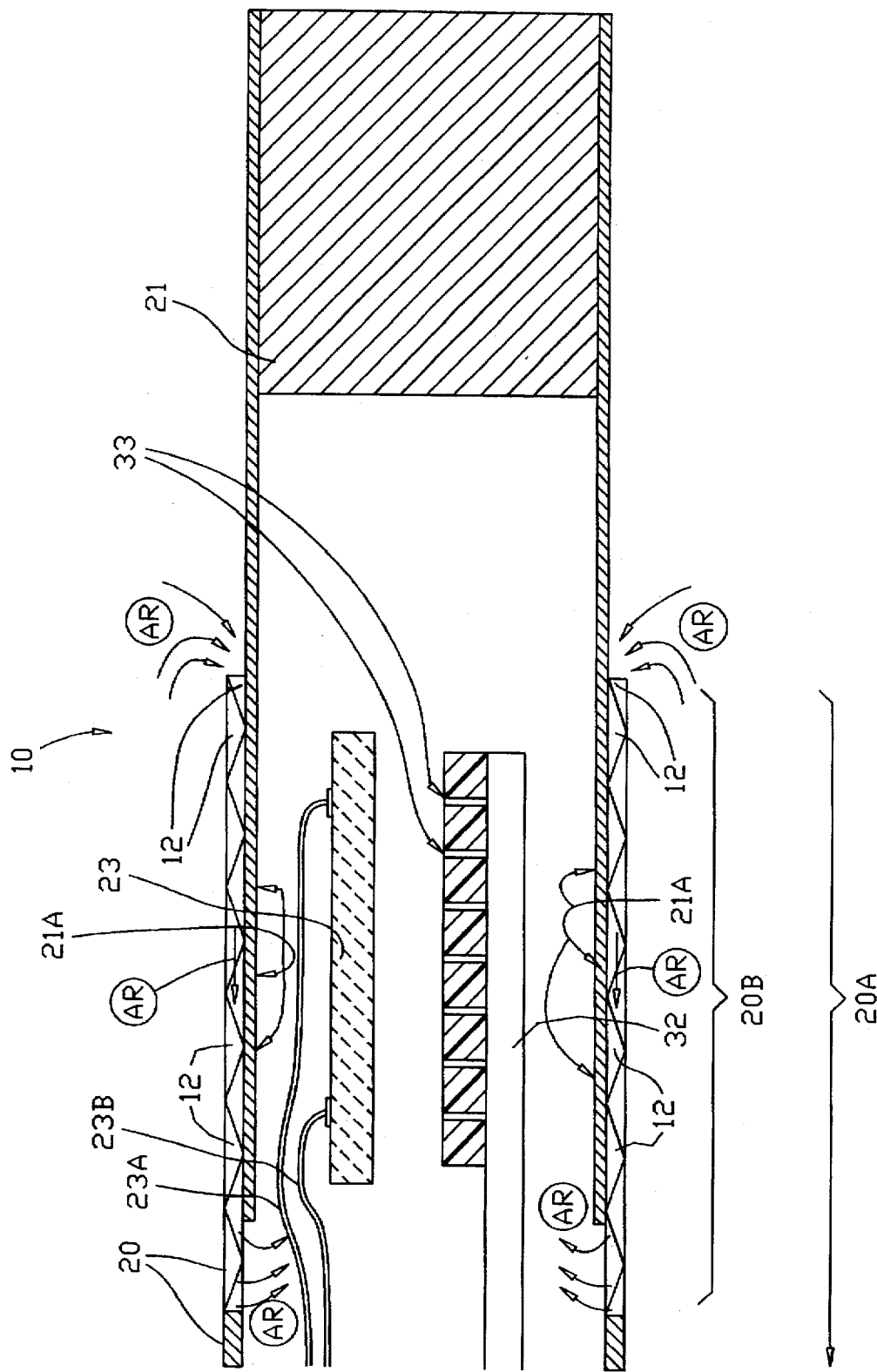
FIG. 3A is a cross-sectional view of the electrical smoking article of FIG. 1, taken from line 3A—3A of FIG. 1.
Figure 3B:
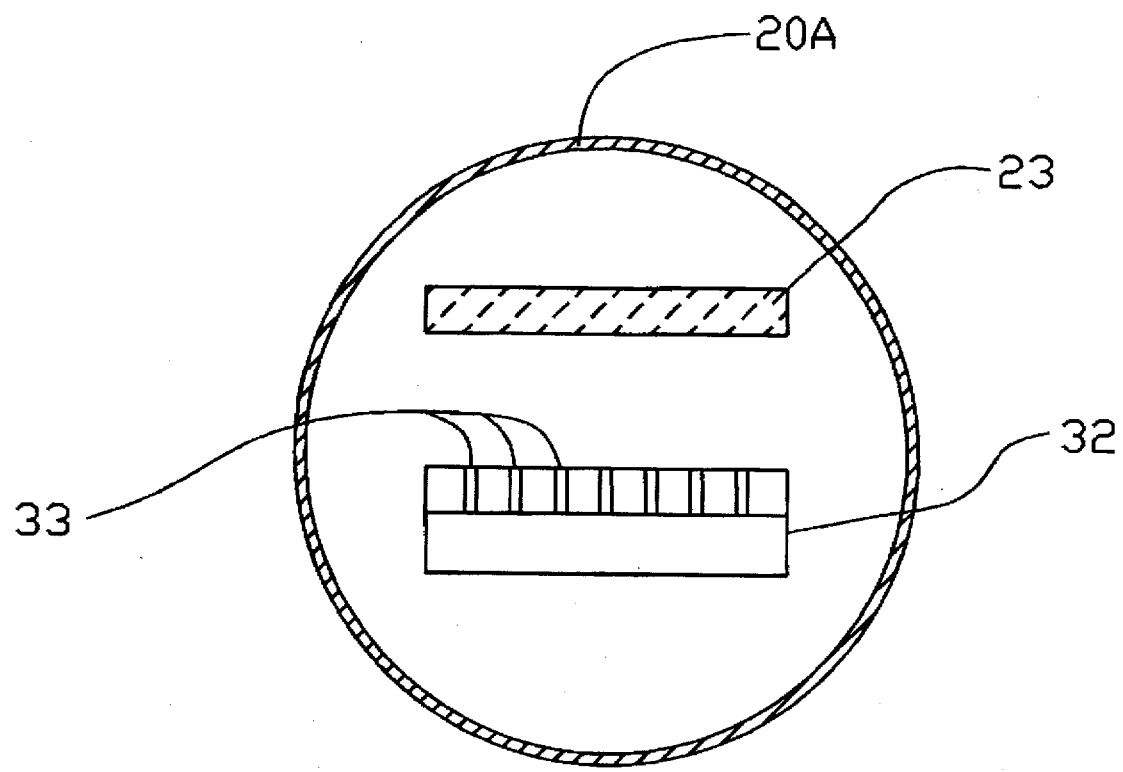
FIG. 3B is a radial cross-sectional view of the electrical smoking article of FIG. 1, taken from line 3B—3B of FIG. 2.

As shown in FIG. 3A, disposable filter insert 21 includes wall portion 21A only where aerosol may condense, reducing the condensation of aerosol onto permanent structural components of article 10. Subsequent reheating of such condensation can produce undesirable compounds causing off-tastes to be delivered to a smoker. In accordance with the present invention, wall portion 21A substantially surrounds heater 23 and liquid jet delivery system 32 and therefore minimizes such condensation. Replacing disposable filter insert 21 with a fresh filter insert reduces the effects of aerosol condensation in the present invention.

In accordance with the present embodiment, liquid jet delivery system 32 is preferably a "bubble jet" delivery system that operates similarly to bubble jet systems used in ink jet printing technology. FIGS. 4A–4F illustrate the operation of liquid jet delivery system 32.

FIGS. 4A–4F are cross sectional views of liquid jet delivery system 32 in a region adjacent a nozzle 33. Nozzle 33 is defined by chamber 51 having a opening region 53 and bottom region 55. Adjacent bottom region 55 of chamber 51 is resistor 57. Coupled to chamber 51 is liquid supply 59 for filling chamber 51 with liquid tobacco flavor medium. Liquid jet delivery system 32 works as follows.

Figure 4A:
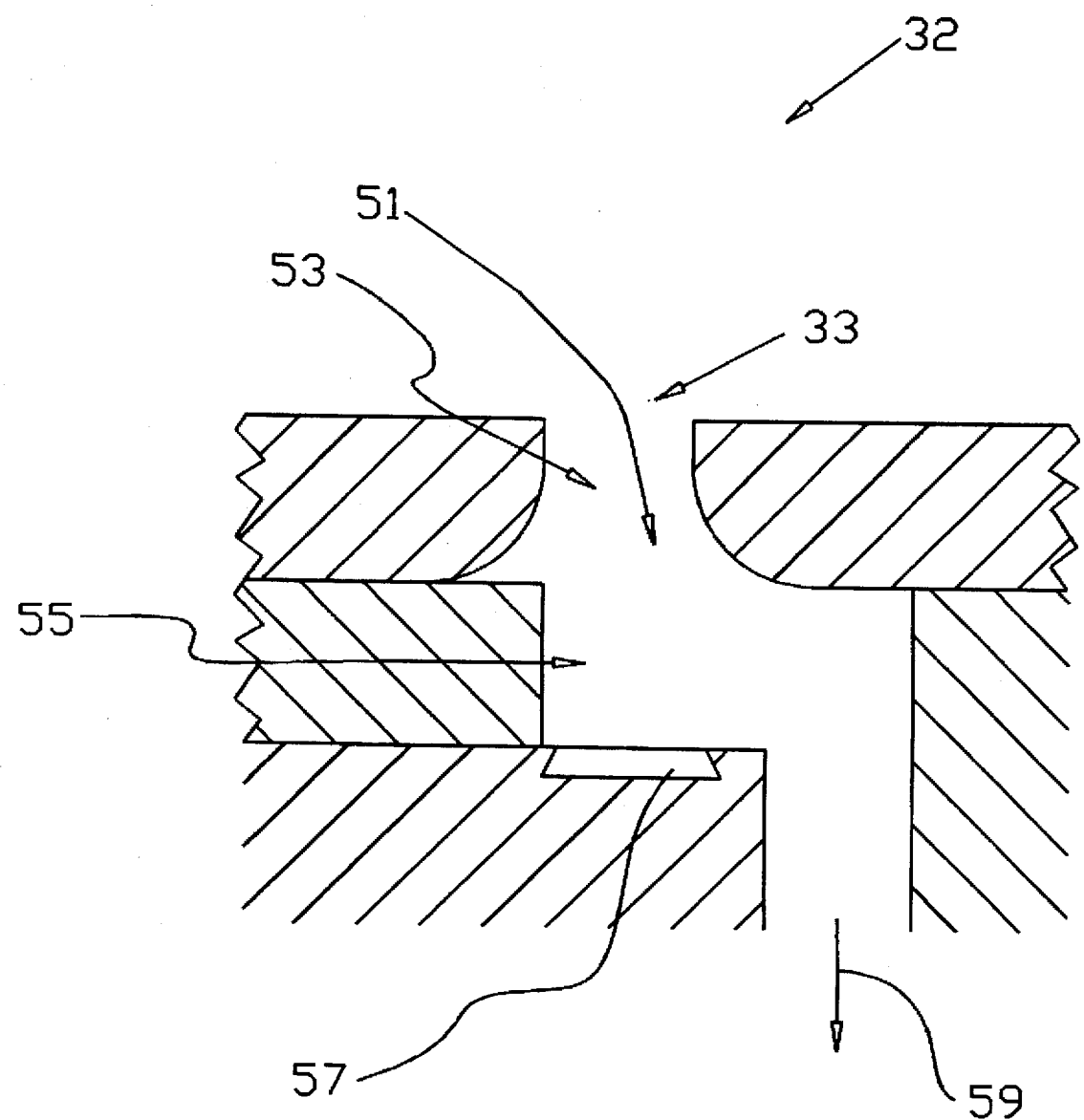
FIGS. 4A–4F are cross-sectional views of the liquid jet delivery system of the electrical smoking article of FIG. 1 illustrating the operation of the delivery system.
Figure 4B:
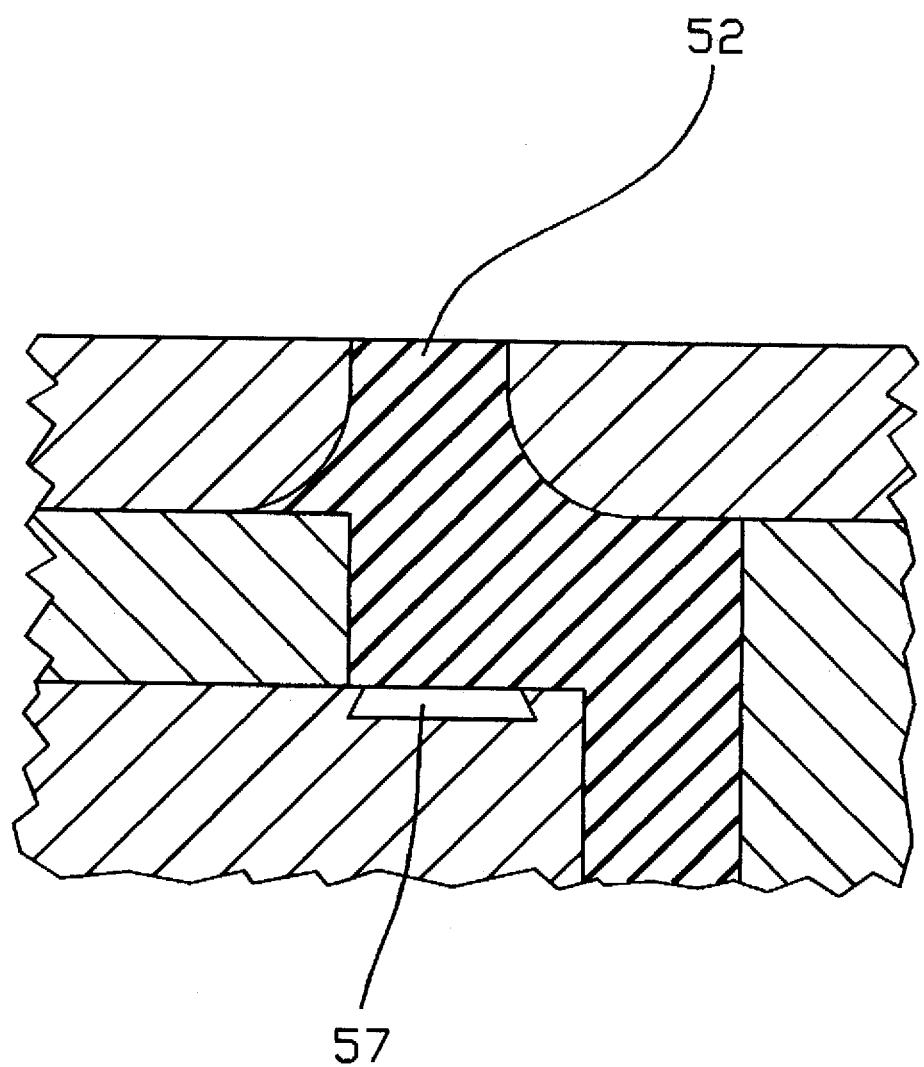
Figure 4C:
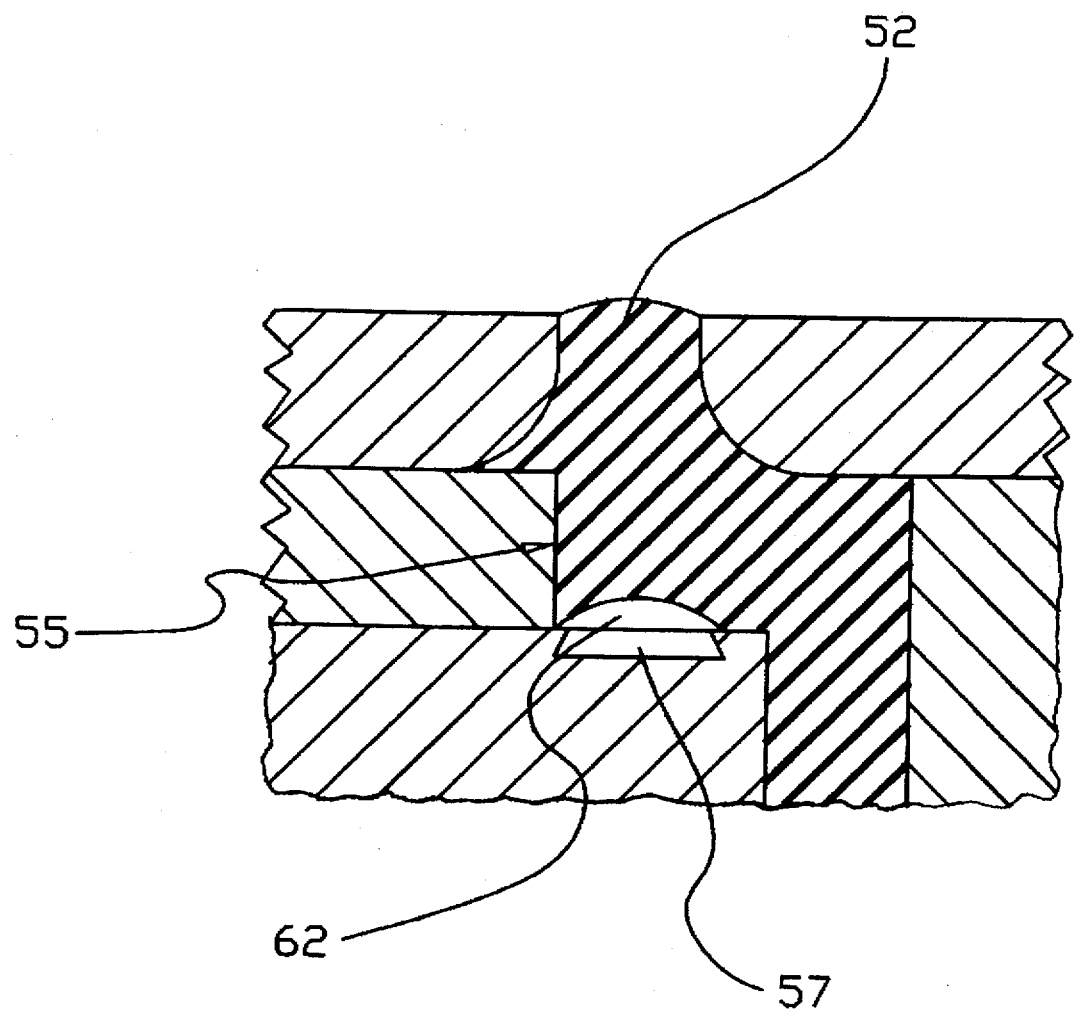
Figure 4D:
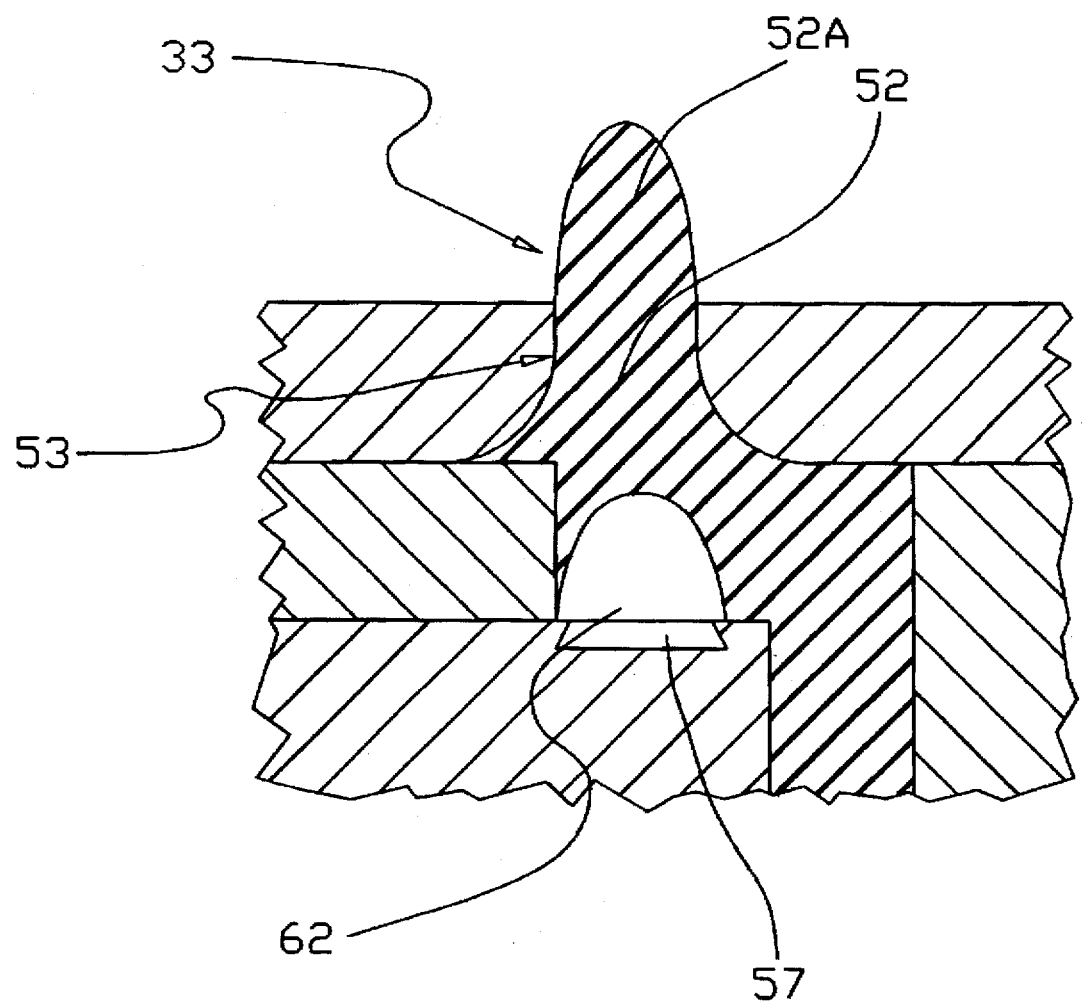
Figure 4E:
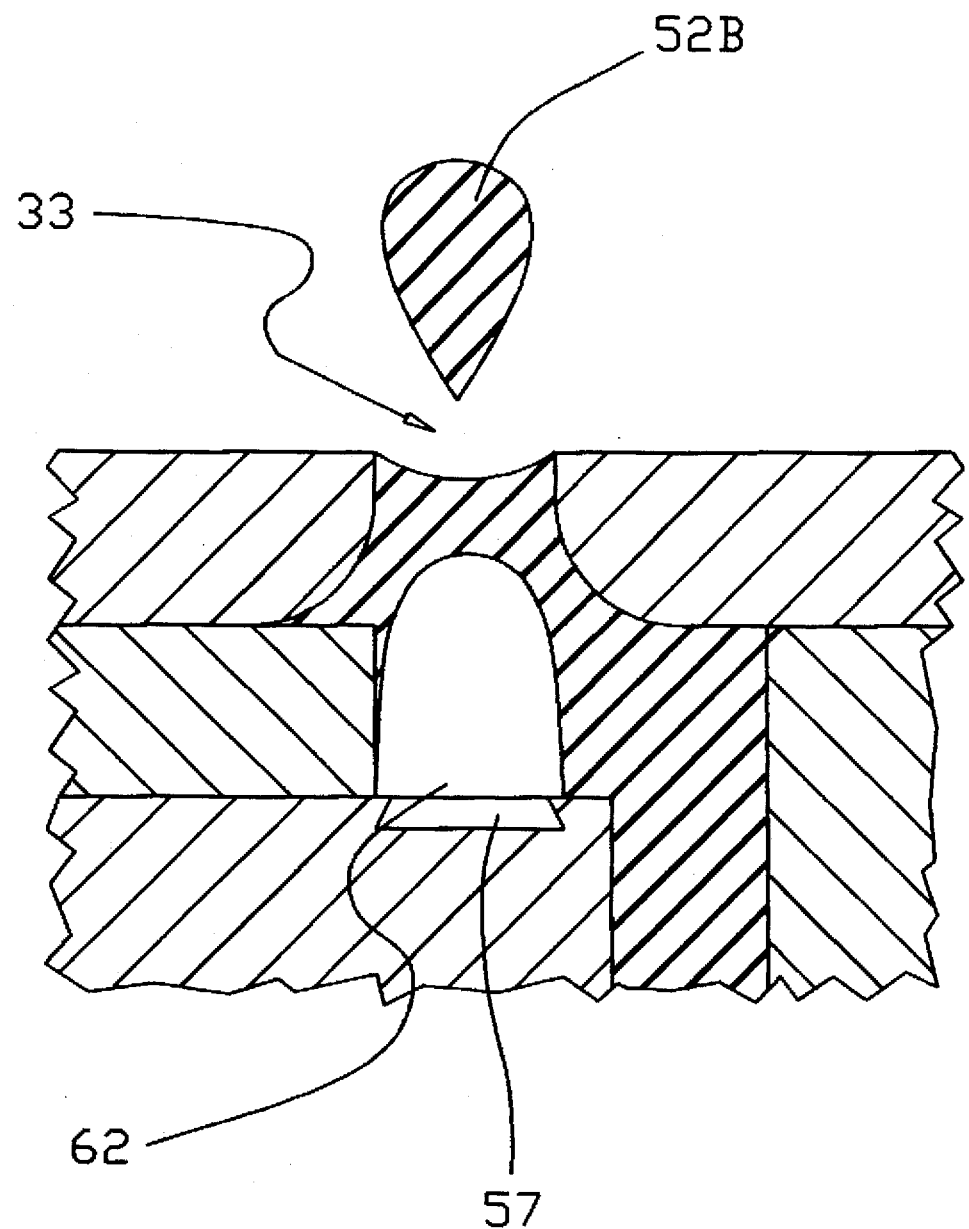
Figure 4F:
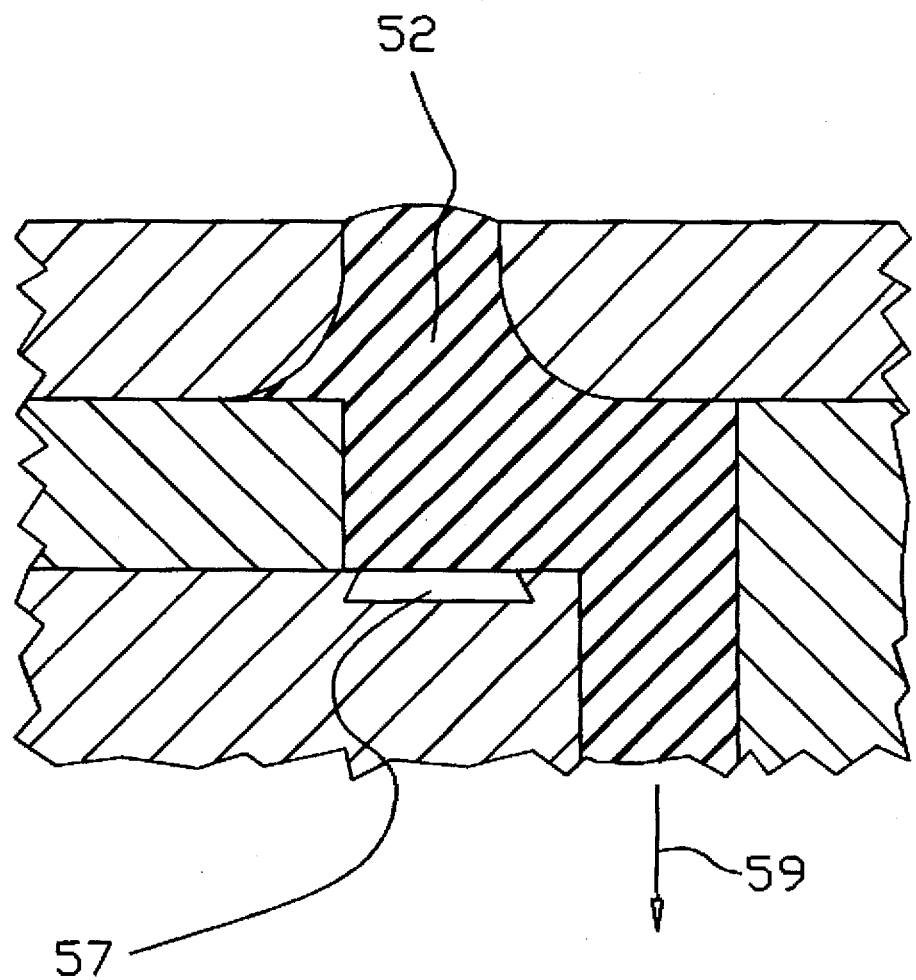

As shown in FIG. 4B, liquid supply 59 is adapted to fill chamber 51 with liquid tobacco flavor medium 52. As shown in FIG. 4C, resistor 57 is used to heat a thin layer of liquid medium 52 in bottom region 55 of chamber 51. The liquid boils and forms a bubble 62 of vapor. As shown in FIG. 4D, vapor bubble 62 expands upward towards opening region 53 of chamber 51 to form a portion 52A of liquid medium 52 which protrudes out of nozzle 33. This expansion forces liquid medium 52 through nozzle 33. As shown in FIG. 4E, upon further expansion of vapor bubble 62, protruding portion 52A overcomes the surface tension of liquid medium 52 in chamber 51 to form a droplet 52B that jets away from nozzle 33. As shown in FIG. 4F, as resistor 57 cools, the vapor bubble collapses and the resulting suction pulls fresh liquid medium 52 from liquid supply 59 into chamber 51. The above process is repeated if resistor 57 is again heated.

The total amount of liquid delivered to the heater per puff will of course depend upon the size and number of nozzles employed in the jet delivery system in addition to the number of droplets released per puff. Preferably, the total amount of liquid delivered to the heater, per puff, is in the range from about 1 mg to about 10 mg, to provide a heated condensation aerosol having a mass in the range from about 0.05 mg to about 3.5 mg, as in conventional cigarettes. Accordingly, liquid jet delivery system 32 preferably includes about 10 to 100 nozzles, more preferably, 30 to 50 nozzles, over an area of approximately 15 mm$^2$ to approximately 25 mm$^2$.

In accordance with the present invention, because the tobacco flavor medium presented to the heater is in liquid form, less tobacco flavor medium is wasted than would otherwise be the case if the tobacco flavor medium were in solid form. The amount of liquid delivered to the heater is controlled so that substantially no excess liquid is delivered beyond that needed to generate the desired amount of tobacco flavor substance for consumption by the smoker. Because excess tobacco flavor medium can serve as a heat sink, the present invention also minimizes the power consumption of the article by minimizing the exposure of the heater to unheated tobacco flavor medium.

Because the electrical smoking article of the present invention includes a single heater, instead of a plurality of heaters, the control circuitry for operating the article can be simplified. For example, the control circuitry discussed in above-incorporated U.S. Pat. No. 5,060,671 includes a BCD-to-decimal decoder for activating, under control of a logic circuit, a particular one of a plurality of heaters. Control circuit 24 of the present invention does not require the use of such a decoder if only one heater is employed. Thus, the control circuitry can be simplified.

Preferably, control circuit 24 includes the features described in above-incorporated U.S. patent application Ser. No. 07/943,504, except for the BCD-to-decimal decoder. For example, it is preferably that control circuit 24 include a logic circuit, voltage detector circuit and timing network circuit as described therein. The purpose of the logic circuit is to control the overall operation of control circuit 24. The purpose of the voltage detector circuit is to monitor the voltage of power source 22 and to provide a signal to the logic circuit indicative of the need for recharging or, during recharging, indicative of the completion of recharging. The purpose of the timing network circuit is to provide a shut-off signal to the logic circuit after the heater has been activated for a predetermined time period, depending upon the amount of energy that is delivered to the heater.

Of course, other control circuits than those described in above-incorporated U.S. patent application Ser. No. 07/943,504 can be used in the electrical smoking article of the present invention, if desired.

Thus, a liquid jet delivery system for an electrical smoking article has been described which is capable of delivering a predetermined amount of liquid tobacco flavor medium onto a heater surface under electronic control.

Figure 5:
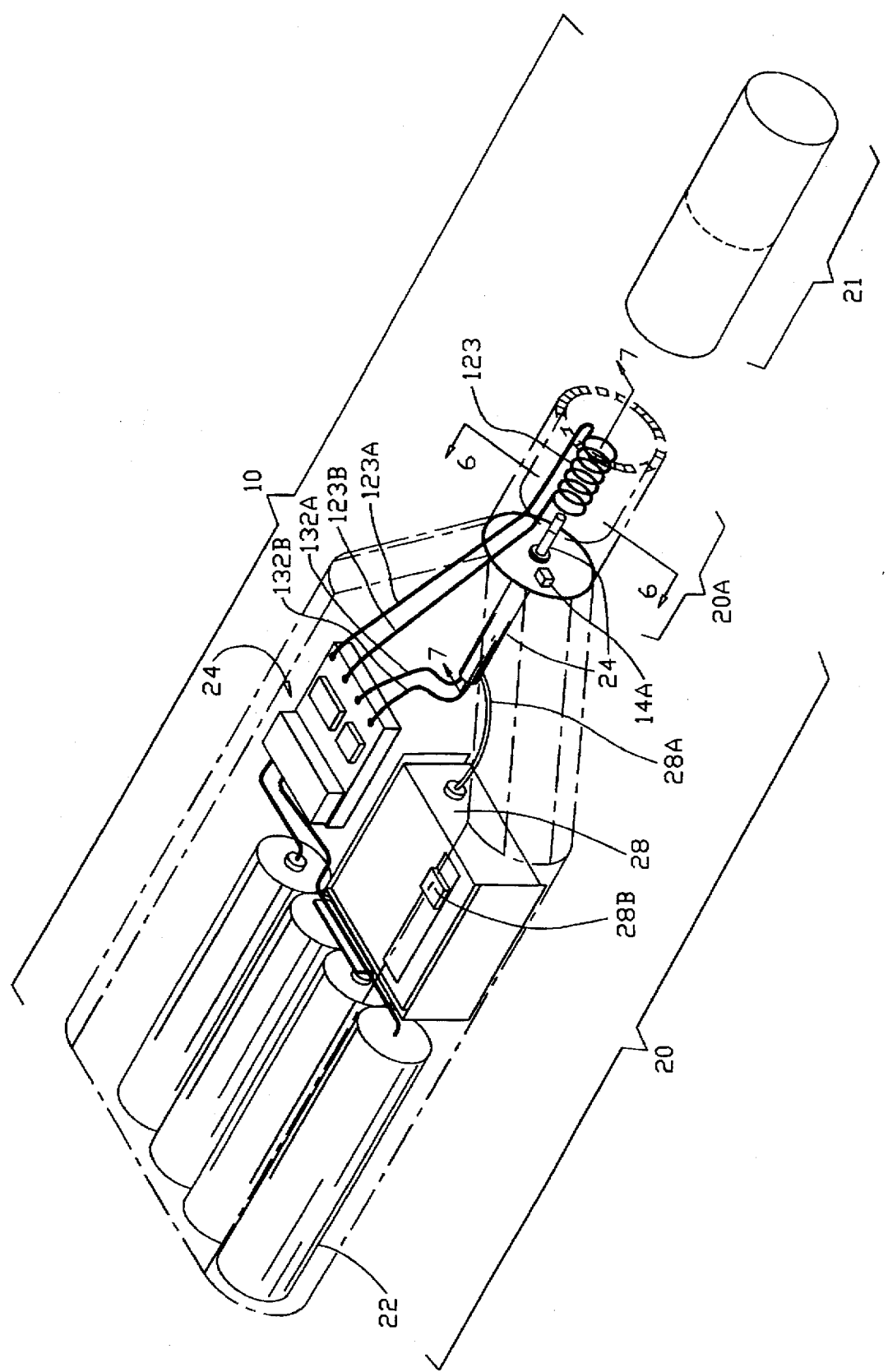
FIG. 5 is a partially fragmentary exploded perspective view of a second preferred embodiment of an electrical smoking article of the present invention.
Figure 6:
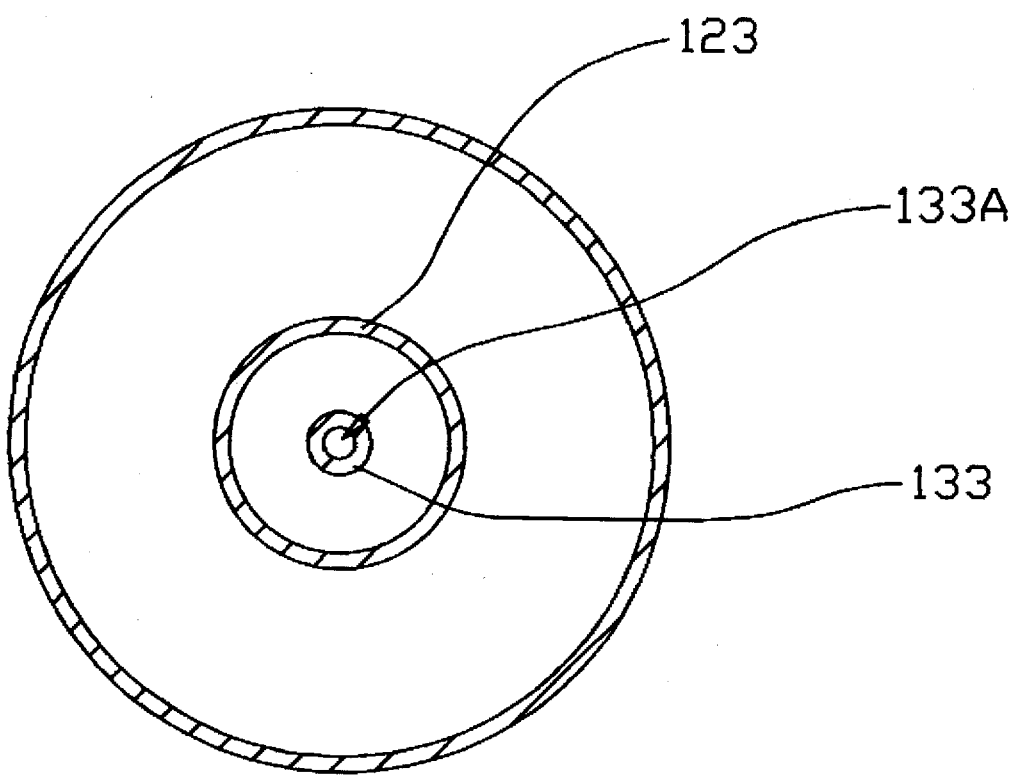
FIG. 6 is a radial cross-sectional view of the electrical smoking article of FIG. 5, taken from line 6—6 of FIG. 5.
Figure 7:
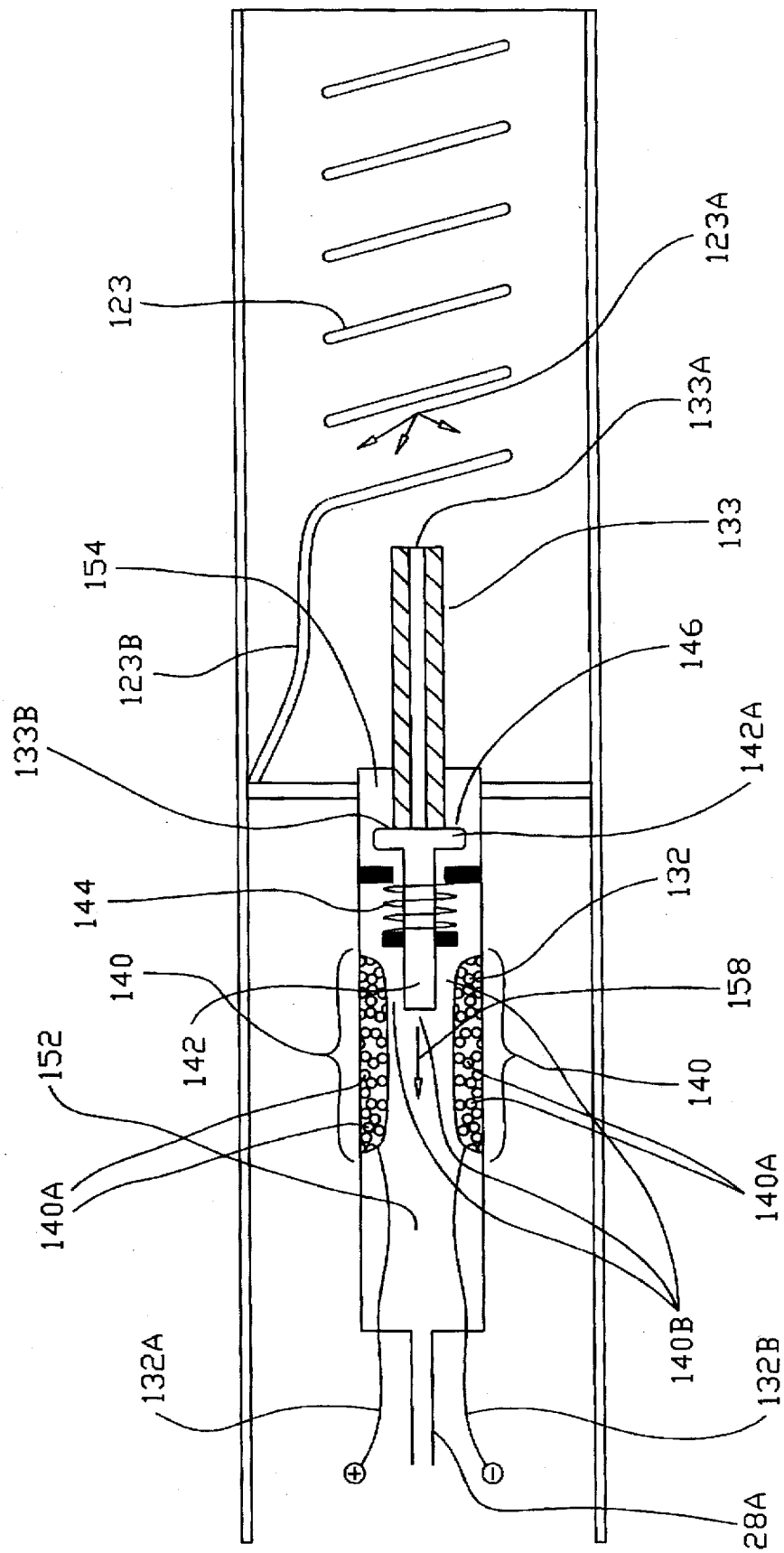
FIG. 7 is a cross-sectional view of the electrical smoking article of FIG. 5, taken from line 7—7 of FIG. 5.

A second preferred embodiment of an electrical smoking article 100 according to the present invention is shown in FIGS. 5–7. Article 100 is similar to article 10 shown in FIGS. 1–4 except that liquid jet delivery system 32 and heater 23 of article 10 have been replaced with valve delivery system 132 and heater 123, as shown in FIGS. 5–7. Valve delivery system 132 employs a nozzle 133 having an opening 133A oriented toward center region 123A of heater 123. Upon exiting opening 133A, a droplet of liquid tobacco flavor medium becomes heated to generate an aerosol which is then drawn through disposable filter insert 21 for delivery to the smoker.

With reference to FIG. 7, a preferred embodiment of valve delivery system 132 is described. Liquid delivery tube 28A fills chambers 152 and 154 with liquid tobacco flavor medium (not shown). Valve delivery system 132 includes plunger 142 having a seat 146 for forming a liquid seal with end 133B of nozzle 133. Spring 144 is used to maintain the valve closed when not electrically activated. Plunger 142 is pulled in direction 158 by solenoid action. Plurality of wires 140A are wound to form coil 140 for generating a magnetic field in region 140B. Upon the application of a potential across leads 132A and 132B, coil 140 is energized and plunger 142 is pulled in direction 158. As a result, the liquid seal is opened to allow the liquid tobacco flavor medium in chamber 154 to exit the valve through end 133B of nozzle 133. Valve 132 closes when coil 140 is de-energized.

In accordance with the present embodiment, a preferred valve delivery system 132 is model INKX0500000AC (8VDC, 0-10PSI) drop-on-demand microvalve, available from The Lee Company of Westbrook, Conn. This particular microvalve has a nozzle opening diameter of about 0.7 mm and has a solenoid that can be driven with a voltage waveform of less than 20 volts peak, for periods of up to about 20 milliseconds, to provide adequate liquid flow rates for use in the electrical smoking article of the present invention.

Thus, a second preferred embodiment of an electrical smoking article which includes a liquid delivery system has been described. The liquid delivery system employs solenoid action to delivery a predetermined quantity of a liquid tobacco flavor medium towards a heater under electrical control. The total amount of liquid delivered to the heater for a given puff will of course depend upon the size of the opening in the liquid delivery system nozzle and length of time that the solenoid is activated.

Figure 8:
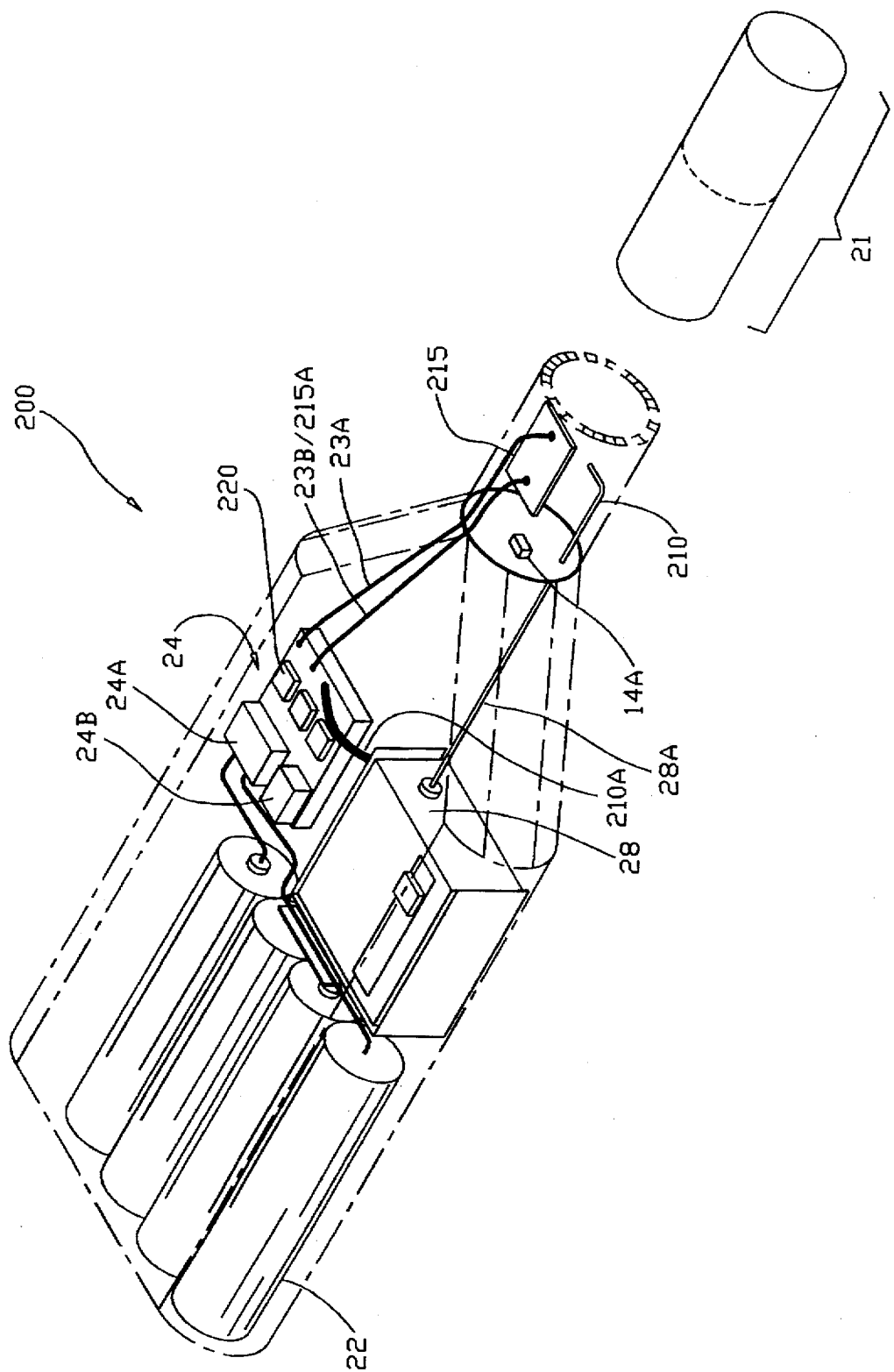
FIG. 8 is a partially fragmentary exploded perspective view of a third preferred embodiment of an electrical smoking article of the present invention.
Figure 9:
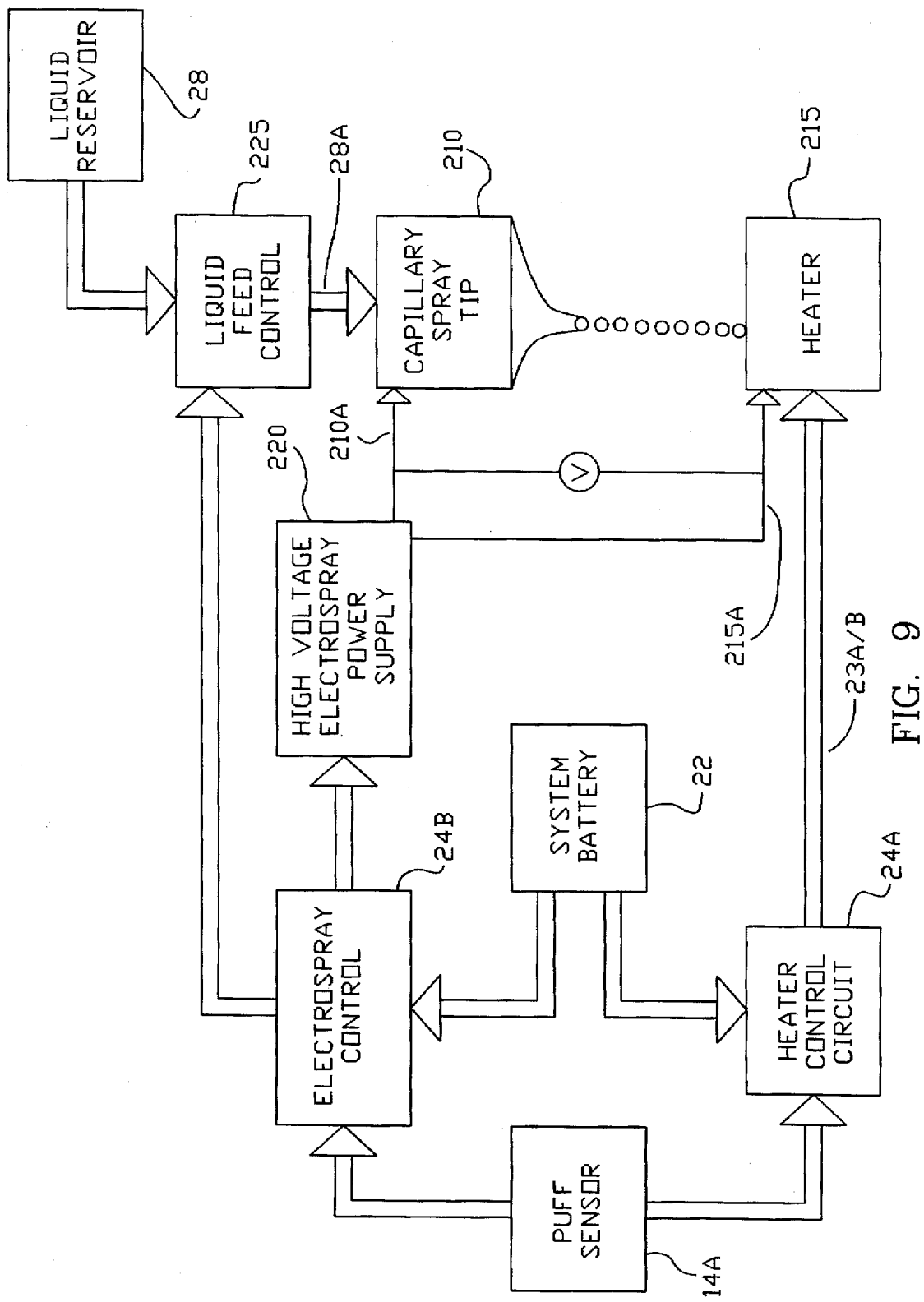
FIG. 9 is a schematic diagram of a preferred embodiment of a control circuit for use in the embodiment of the electrical smoking article shown in FIG. 8.

A third preferred embodiment of an electrical smoking article 200 according to the present invention is shown in FIG. 8. Article 200 is similar to articles 10 and 100 shown in FIGS. 1–7 except the liquid delivery system is an electrospray liquid delivery system. FIG. 9 is a schematic diagram of a preferred embodiment of a control circuit for use in the embodiment of the electrical smoking article shown in FIG. 8.

Article 200 includes capillary spray tip 210 oriented towards heater 215. High voltage power supply 220 is used to provide a high voltage (e.g., about 1,000 volts to about 3000 volts) between spray tip 210 and heater 215. Such a high voltage creates an electrostatic potential between tip 210 and heater 215 that is capable of transferring a liquid droplet from tip 210 to heater 215. Article 200 operates as follows.

AS shown in FIG. 9, sensor 14A (or, in the alternative pushbutton 14) is used to activate heater control circuit 24A and electrospray control circuit 24B, both of which are powered by battery 22. Electrospray control 24B is coupled to high voltage power supply 220 which generates the high voltage potential across capillary tip 210 (through lead 210A) and heater 215 (through lead 215A) in response to smoker activation by sensor 14. Capillary tip 210 is coupled to liquid supply cartridge 28 through optional liquid feed control 225 (not shown in FIG. 8) which is used to control the flow of liquid from supply 28 to tip 210 if needed.

Thus, during smoker activation, electrospray control circuit 24B applies a high voltage potential between tip 210 and heater 215, while heater control circuit 24A energizes heater 215 (through leads 24B). Thereafter, liquid tobacco flavor medium is transferred from liquid supply 28 out through capillary tip 210 to heater 215, where the transferred droplets are heated to generate an aerosol which is then drawn through disposable filter insert 21 for delivery to the smoker.

In accordance with the present embodiment, high voltage power supply 220 is a conventional circuit that steps up the battery voltage to the desired operating voltage (e.g., multiple thousands of volts). The high voltage can be either direct current (DC), of either polarity, or alternating current (AC) and can be applied directly at capillary tip 215 or, if desired, at a location farther up stream at liquid medium cartridge 28 (as shown in FIG. 8). If AC high voltage is used, power supply 220 generally includes chopping circuits for providing the alternating polarity at the chosen frequency. Of course, article 200 must be sufficiently electrically insulated to prevent high-voltage current from flowing outside the capillary tip-heater loop.

If desired, electrostatic control circuit 24B could include conventional timing circuitry (not shown) to initiate and terminate the application of high voltage across tip 215 at fixed times after smoker activation of sensor 14A.

In accordance with the third embodiment, the amount of liquid transferred from the liquid reservoir to the heater surface upon application of a given electrostatic potential will be determined by the resistance to flow of the capillary tube, the capillary tip dimensions, the distance between the tip and the heater, the surface tension of the liquid and the viscosity of the liquid.

For example, with a water-filled 1 mm glass tube having a capillary tip diameter of 200 microns, the flow rate of relatively large, discrete water droplets was approximately 10 microliters per second with a 3,000 volt DC electrostatic potential applied across a distance of 10 mm. With a 50 micron capillary tip at 5,000 volts across 15 mm, the flow was reduced to approximately 2 microliters per second with the spray approaching the appearance of an aerosol, as opposed to a spray of larger discrete droplets. Electrical currents required to provide the above flow rates were typically below 30 microamps.

Thus, a third preferred embodiment of a liquid delivery system for an electrical smoking article has been described which is capable of delivering a predetermined amount of liquid tobacco flavor medium towards a heater under electrical control.

Although the electrical smoking article of the present invention has been discussed above with respect to particular liquid delivery systems and particular heater geometries, it will be apparent that other methods of transferring the liquid tobacco flavor medium from the reservoir to the heater can be used as well.

Thus, it is seen that an electrically-heated smoking article is provided in which the tobacco flavor medium is a liquid. The electrical smoking article includes an electrical heater in conjunction with a means for transferring a predetermined amount of a tobacco flavor generating liquid to the heater.

One skilled in the art will appreciate that the present invention can be practiced by other than the described embodiments, which are presented for purposes of illustration and not of limitation, and the present invention is limited only by the claims which follow.

What is claimed is:

1. An electrical smoking article for delivering to a smoker a tobacco flavor substance, said article comprising:
   an electrical heater;
   a tobacco flavor medium delivery system in a liquid transfer relationship with said heater, said delivery system comprising:
   (a) inlet means for coupling to a supply of liquid tobacco flavor medium;
   (b) outlet means having one or more openings for dispensing liquid tobacco flavor medium in droplet form onto said heater;
   (c) means coupled between said inlet means and said outlet means, said coupled means for transferring a predetermined amount of liquid tobacco flavor medium from said supply of liquid tobacco flavor medium to said outlet;
   a source of electrical energy;
   control means for applying said electrical energy to said heater to generate heat and for activating said tobacco flavor medium delivery system such that upon activation of said delivery system, said delivery system dispenses said predetermined amount of liquid tobacco flavor medium in droplet form onto said heater, said dispensed tobacco flavor medium being heated sufficiently to release an aerosol therefrom which includes a predetermined quantity of tobacco flavor substance; and
   means for drawing air together with said released aerosol from the electrical smoking article upon puffing action by a smoker;
   wherein said control means applies sufficient energy to said heater to achieve a temperature in said heater in the range of about 300° C. to about 450° C. during a puff and
   wherein said means for drawing air together with said released aerosol includes a disposable filter insert and air channels arranged to admit air into said electrical smoking article.

2. The article of claim 1 wherein the transferring means comprises a valve.

3. The article of claim 2 wherein the valve includes a solenoid for actuating transfer of the liquid tobacco flavor medium.

4. The article of claim 3 wherein the heater comprises a coil of wire forming a center region and wherein the outlet means dispenses liquid tobacco flavor medium onto said center region.

5. The article of claim 4 wherein each of the one or more openings has an opening diameter of less than about 1 mm.

6. The article of claim 3 wherein transfer is actuated by applying a voltage waveform to said solenoid for a predetermined period of time.

7. The article of claim 6 wherein said voltage waveform is substantially a DC voltage signal.

8. The article of claim 7 wherein said DC voltage signal is less than about 20 volts DC.

9. The article of claim 6 wherein said predetermined period of time is in a range from about 1 ms to about 20 ms.

10. The article of claim 1 wherein the outlet means comprises a capillary tip and the transferring means comprises:
   an electrostatic potential delivery system adapted to have a high-voltage potential applied between said heater and said capillary tip for transferring the liquid tobacco flavor medium therebetween.

11. The article of claim 10 wherein the high-voltage potential is in the range from about 2000 volts to about 6000 volts.

12. The article of claim 10 wherein said high-voltage potential is substantially a DC voltage.

13. The article of claim 10 wherein said high-voltage potential is substantially an AC voltage.

14. The article of claim 10 wherein said capillary tip has a diameter in the range from about 20 micrometers to about 250 micrometers.

15. The article of claim 1, wherein aerosol is released from the same heater during each activation of said delivery system.

16. The electrical smoking article as claimed in claim 1 wherein air together with aerosol is drawn in a first direction through said filter insert, said outlet means dispensing liquid flavor medium in a second direction transverse to said first direction.

17. The electrical smoking article of claim 1 further comprising a puff sensor in communication with said control means.

18. The electrical smoking article of claim 1, wherein said supply of liquid flavor medium comprises a cartridge.

19. The electrical smoking article of claim 1, wherein said electrical heater consists of a single heater element.

20. The electrical smoking article of claim 1, wherein the tobacco flavor medium delivery system delivers liquid tobacco flavor medium at a rate per puff in the range of from about 1 milligram to about 10 milligram.

21. The electrical smoking article of claim 20, wherein the heater element is adapted to achieve a temperature in the range of about 300° C. to about 450° C. during a puff.

22. An electrical smoking article for delivering to a smoker a tobacco flavor substance, said article comprising:
   an electrical heater;
   a tobacco flavor medium delivery system in a liquid transfer relationship with said heater, said delivery system comprising:
   (a) inlet means for coupling to a supply of liquid tobacco flavor medium;
   (b) outlet means having one or more openings for dispensing liquid tobacco flavor medium in droplet form onto said heater;
   (c) means coupled between said inlet means and said outlet means, said coupled means for transferring a predetermined amount of liquid tobacco flavor medium from said supply of liquid tobacco flavor medium to said outlet;
   a source of electrical energy;
   control means for applying said electrical energy to said heater to generate heat and for activating said tobacco flavor medium delivery system such that upon activation of said delivery system, said delivery system dispenses said predetermined amount of liquid tobacco flavor medium in droplet form onto said heater, said dispensed tobacco flavor medium being heated sufficiently to release an aerosol therefrom which includes a predetermined quantity of tobacco flavor substance; and
   means for drawing air together with said released aerosol from the electrical smoking article upon puffing action by a smoker;

wherein the transferring means comprises a bubble jet delivery system.

23. The article of claim 22 wherein the bubble jet delivery system includes one or more chambers and one or more integral heaters each positioned respectively at a bottom of a chamber for transferring the liquid tobacco flavor medium.

24. The article of claim 23 wherein said heater has a substantially flat surface and wherein said outlet means dispenses liquid tobacco flavor medium onto said flat surface.

25. The article of claim 23 wherein each of the one or more integral heaters comprises a resistor.

26. The article of claim 25 wherein transfer is actuated by applying a potential to said one or more resistors for a predetermined period of time.

27. The article of claim 26 wherein said potential is substantially a DC voltage signal.

* * * * *